Yukawa et al.

United States Patent [19]

[11] 4,326,029
[45] Apr. 20, 1982

[54] PROCESS FOR PRODUCTION OF L-ASPARTIC ACID

[75] Inventors: Hideaki Yukawa; Terukazu Nara; Yoshihiro Takayama, all of Ibaraki, Japan

[73] Assignee: Mitsubishi Petrochemical Co., Ltd., Tokyo, Japan

[21] Appl. No.: 177,044

[22] Filed: Aug. 11, 1980

[30] Foreign Application Priority Data

Aug. 10, 1979 [JP] Japan ............................... 54/101820

[51] Int. Cl.$^3$ ............................................. C12P 13/20
[52] U.S. Cl. ................................. 435/109; 435/172; 435/232; 435/840
[58] Field of Search ............... 435/109, 172, 116, 232

[56] References Cited

U.S. PATENT DOCUMENTS 3,907,641  9/1975  Nakayama et al. ............. 435/116 X
3,970,519  7/1976  Tsuchida et al. .................... 435/116
4,000,040 12/1976  Tsuchida et al. .................... 435/109

*Primary Examiner*—Lionel M. Shapiro
*Attorney, Agent, or Firm*—Sughrue, Mion, Zinn, Macpeak and Seas

[57] ABSTRACT

A process for producing L-aspartic acid economically and efficiently from fumaric acid or a salt thereof and ammonia or an ammonium salt using a cultured product obtained by aerobically culturing an microorganism belonging to the Genus Brevibacterium and having resistance to α-amino-n-butyric acid.

2 Claims, No Drawings

PROCESS FOR PRODUCTION OF L-ASPARTIC ACID

BACKGROUND OF THE INVENTION

1. Field of the Invention

The present invention relates to a process for efficiently producing L-aspartic acid from fumaric acid or a salt thereof and ammonia or an ammonium salt as starting materials, by utilizing the reaction of an enzyme present in an aerobic culture of a microorganism belonging to the Genus Brevibacterium and having resistance to α-amino-n-butyric acid.

2. Description of the Prior Art

L-Aspartic acid is known to be present in protein as one of the important amino acids, and is used in medicines and as a food additive.

Heretofore, it has been known that aspartase, which can be obtained from cells of Escherichia coli, is an enzyme which dominates the reaction to form L-aspartic acid from fumaric acid and ammonia. More recently, methods have become known for producing L-aspartic acid from fumaric acid and ammonia by a fermentation culture method using various microorganisms.

In the conventional fermentation culture method, L-aspartic acid is produced from fumaric acid and ammonia using aspartase in microorganisms, and therefore it has been an important factor for production on a commercial scale to obtain microorganisms having strong aspartase activity; however, separation of microorganisms which satisfy such purposes from nature is accompanied by many difficulties, thus inhibiting the industrial use of such methods.

SUMMARY OF THE INVENTION

Accordingly, the present invention is a process for producing L-aspartic acid from fumaric acid or a salt thereof and ammonia or an ammonium salt using a cultured product obtained by aerobically culturing a microorganism belonging to the Genus Brevibacterium and having resistance to α-amino-n-butyric acid.

As a result of intensive studies, it has now been found that impartation of resistance to α-amino-n-butyric acid to microorganisms belonging to the Genus Brevibacterium greatly enhances their aspartase activity, i.e., their ability to biosynthesize L-aspartic acid from fumaric acid and ammonia and the present invention has thus been accomplished.

DETAILED DESCRIPTION OF THE INVENTION

The present invention has been achieved as a result of the success in developing a method of growing strains which are advantageous for a commercial production of L-aspartic acid, and, according to the process of the invention L-aspartic acid may thereby be obtained economically and efficiently.

the microorganisms used in the present invention are those belonging to the Genus Brevibacterium and having resistance to α-amino-n-butyric acid, and they are not limited only to the microorganisms which have been artificially imparted with the resistance mechanism but also extended to those which have acquired such mechanism through accidental variation in nature.

A representative strain used in the present invention is Brevibacterium flavam MJ-233-AB-41 (FERM-P No. 3812). This strain may be derived from Brevibacterium flavam MJ-233 (FERM-P No. 3068) as an α-amino-n-butyric acid resistant strain by, for example, the following procedures.

Brevibacterium flavam MJ-233 was caused to mutate by treating it with a chemical agent such as N-methyl-N'-nitro-N-nitrosoguanidine having a concentration of, for example, about 50 to 500 μg/ml, for example, about 1 to 60 minutes, and the thusobtained organism suspension was cultured in a plate culture (urea 0.2%, ammonium sulfate 0.7%, $KH_2PO_4$ 0.05%, $K_2HPO_4$ 0.05%, $MgSO_4.7H_2O$ 0.05%, NaCl 2 mg/l, $CaCl_2.2H_2O$ 2 mg/l, $FeSO_4.7H_2O$ 2 mg/l, $MnSO_4.4$-$6 H_2O$, $ZnSO_4.7$-$H_2O$ 2 mg/l, biotin 200 μg/l, thiamine hydrochloride 100 μg/l, α-amino-n-butyric acid 1.0%, agar 2.0% and ethanol 3% by volume (added after sterilization)) at 30° C. for several days, after which the large colony formed was separated to obtain the resistant variant.

The mycological properties and reasons for the taxonomical identification of the Brevibacterium flavam MJ-233-AB-41 variant obtained are as follows:

Mycological properties

I. Observed microscopic properties

Brevibacillus of oval or rod form with approximate dimensions of 0.6 to 0.8×1.0×2.4μ, generally formed as V-shaped pairs, although fence-like forms are also observed. These bacillus are also observed to be gram positive, show no spore formation, no motility, no capsule formation and are not acid-fast.

II. Culture properties
1. Bouillon agar colony:
    Circular, flat surface, colony almost flat or slightly raised, periphery somewhat wavy, yellow, opaque and somewhat bright.
2. Bouillon agar slant culture:
    Medium growth, filamentous, and yellow.
3. Bouillon liquid culture:
    Medium growth, slime observed and no turbidity.
4. Bouillon gelatin stab culture:
    Growth good on the surface, but internal growth slight and filamentous.

III. Growth conditions
1. Growth temperature: useful temperature range 15°–40° C., optimum temperature 30°–37° C.
2. pH: useful range 1–10 optium pH 7–8.
3. Behavior with respect to oxygen: aerobic
4. Utilization of ammonium salt: yes
5. Utilization of urea: yes
6. Utilization of nitrate: yes IV. Physiological properties, etc.
1. It does not liquefy gelatin.
2. It does not change litmus milk.
3. Reduction of nitrate: positive
4. Formation of indole: negative
5. Formation of hydrogen sulfide: negative
6. Hydrolysis of starch: negative
7. Ammonia formation from peptone: positive
8. Vorges-Proskauer reaction: negative
9. Methyl Red test: positive (weak)
10. Cathalase: positive
11. Urease: positive
12. Formation of acid from hydrocarbonates:
    Acid formed but no gas formed from glucose, saccharose, trehalose, maltose and salicin. Neither acid nor gas formed from arabinose, xylose, lactose, rhamnose, raffinose, mannitol, dulcitol, inositol and adonitol.
13. Vitamin requirement: Biotin is required.

Changes in Gram-staining, morphological change or ramification of cells with proliferation were not observed.

In addition, the relative degrees of growth of the afore-described *Brevibacterium flavam* MJ-233-AB-41 and its parent strain, *Brevibacterium flavam* MJ-233, against α-amino-n-butyric acid are set forth in the following Table 1 in which all of the percentages are by weight.

TABLE 1

(Notes 1 and 2)

| Amount of α-Amino-n-butyric Acid Added (%) | Parent Strain MJ-233 | α-Amino-n-butyric Acid Resistant Strain MJ-233-AB-41 |
|---|---|---|
| 0 | 100 | 100 |
| 1.0 | 50 | 60 |
| 1.5 | 30 | 50 |
| 2.0 | <5 | 40 |

Notes:
1. The figures in columns 2 and 3 of Table 1 are expressed as the degree of growth measured as $O.D._{610}$ relative to that obtained when no α-amino-n-butyric acid was added as 100 (for measurement of the absorbance, see Agricultural and Horticultural Chemistry, Tokyo University, Agricultural Department, Vol. 1, p. 212, published by Asakura Shoten (1969)).
2. Composition of the culture used and culturing method: 10 ml of a medium composed of urea (0.2%), ammonium sulfate (0.7%), $KH_2PO_4$ (0.05%), $K_2HPO_4$, (0.05%), $MgSO_4 \cdot 7H_2O$ (0.05%), yeast extract (0.01%), Casamino acid (0.01%), $FeSO_4 \cdot 7H_2O$ (2 mg/l), $MnSO_4 \cdot 4$–6 $H_2O$ (2 mg/l), NaCl (2 mg/l), $CaCl_2 \cdot 2H_2O$ (2 mg/l), $ZnSO_4 \, 7H_2O$ (2 mg/l), biotin (200 μg/l) and thiamine hydrochloride (100 μg/l), and containing α-amino-n-butyric acid in the amount shown in Table 1 was poured into a large test tube having a diameter of 24 mm, sterilized at 120° C. for 10 minutes, inoculated with *Brevibacterium flavum* MJ-233-AB-41 and added with 0.3 ml (3% by volume) of ethanol under aseptic conditions, followed by culturing with shaking at 30° C. for 3 days.

The difference in degree of resistance between the parent strain and the α-amino-n-butyric acid resistant strain is not critical, and any strain which has improved resistance to α-amino-n-butyric acid as compared with its parent strains is considered to be a resistant strain.

The α-amino-n-butyric acid resistant strain according to the present invention has preferably a relative degree of growth as defined below of at least 15 when a 2% α-amino-n-butyric acid is added to a culture medium and cultured with shaking at 30° C. for 3 days.

$$\text{Relative degree of growth} = \frac{\text{Degree of growth when 2\% α-amino-n-butyric acid is added}}{\text{Degree of growth when 2\% α-amino-n-butyric acid is not added}} \times 100$$

Instead of the treatment with the chemical agent, *Brevibacterium flavam* MJ-233 may be caused to mutate by irradiating with ultraviolet light.

The culture medium composition, e.g. carbon sources, nitrogen sources, inorganic salts, etc., used in the culture of the present invention can be those known in the art, and are not particularly limited.

Carbon sources such as ethanol, methanol, n-paraffins, molasses, etc., may be used alone or as a mixture, and nitrogen sources such as ammonia, ammonium sulfate, ammonium chloride, ammonium nitrate, urea, etc., may be used alone or as a mixture.

Inorganic salts such as potassium monohydrogenphosphate, potassium dihydrogenphosphate, magnesium sulfate, etc., may be added. In addition, if necessary for the growth of cells, other nutrients may be added to the medium, e.g., peptone, bouillon extract, yeast extract, corn steep liquor, Casamino acid, various vitamins, and so forth.

The culture is carried out under aerobic conditions, such as by stirring with aeration, shaking, etc., at a culture temperature of from 20° to 40° C., and preferably at from 25° to 35° C. The pH culture is pH of from 5 to 10, and preferably from 7 to 8, and adjustment of pH of the culture liquid is effected by adding acid or alkali.

The concentration of α-amino-n-butyric acid added is from 0.1 to 5% by weight, and preferably from 1 to 30% by weight.

The concentration of ethanol at the start of culture is from 1 to 50% by volume, and preferably from 2 to 30% by volume. The culture period usually requires from 2 to 8 days, with the optimum period being 4 to 5 days.

Since the cultured product thus-obtained contains highly active aspartase, it can efficiently biosynthesize L-aspartic acid from fumaric acid or a salt thereof, e.g., the sodium salt, potassium salt, etc., and ammonia or an ammonium salt, e.g. ammonium chloride, ammonium carbonate, etc.

The above-mentioned cultured product refers to all the products obtained by culture, that is, not only the culture liquid itself but also the cells contained therein, the destroyed, crushed and self-digested products of such cells, etc.

The method of biosynthesis of L-aspartic acid from fumaric acid or a salt thereof and ammonia or an ammonium salt may be carried out in a conventional manner except that the cultured product of the present invention is used instead of conventional cultured products.

The present invention is more particularly described by the following Example, but the present invention is not limited thereto.

In the Example, the qualitative assay of the L-aspartic acid produced was conducted by comparing Rf values using paper chromatography with those of standard L-aspartic acid product, and for the quantitative assay, a quantitative analytical method for microorganisms utilizing *Leuconostoc mesenterioides* (ATCC No. 8042). See also, for example, *JIKKEN NOGEI KAGAKU* (Experimental Agricultural Chemistry), the first volume, pages 284–285, Tokyo University, Faculty of Agriculture, Department of Agricultural Chemistry, published by Asakura Shobo (1960). Collection of the L-aspartic acid produced was conducted by a conventional method, e.g., isoelectric precipitation, ion-exchange resin chromatography, etc. See, for example, *AMINOSAN HAKKO* (Amino Acid Fermentation), the second volume, pages 129–138, published by Kyoritsu Shuppan (Japan).

EXAMPLE 10 ml each of a medium composed of 4.0 g of urea, 14.0 g of ammonium sulfate, 0.5 g of $KH_2PO_4$, 0.5 g of $K_2HPO_4$, 0.5 g of $MgSO_4 \cdot 7H_2O$, 6 mg of $FeSO_4 \cdot 7H_2O$, 6 mg of $MnSO_4 \cdot 4$–6 $H_2O$, 1.0 g of yeast extract, 1.0 g of Casamino acid, 200 μg of biotin, 100 μg of thiamine and 1 l of tap water was poured into a large test tube of a diameter of 24 mm, sterilized at 120° C. under pressure for 10 minutes, and 0.3 ml of ethanol was added thereto to prepare each preculture medium. Mediums were inoculated with *Brevibacterium flavam* MJ-233 and *Brevibacterium flavam* MJ-233-AB-41 respectively, and cultured with shaking at 30° C. for 2 days. Thereafter, 50 ml amounts of medium having the same composition as the preculture medium above were poured into 500-ml Erlenmeyer flasks and sterilized at 120° C. under pressure for 10 minutes to prepare appropriate culture mediums, which were then inoculated with 1.0 ml of the above preculture liquid and shake cultured at 30° C. for 3 days, followed by centrifugal separation (3,000 rpm for 15 minutes) to collect the cells.

Separately, 10 g of fumaric acid was added to 50 ml of water, adjusted to pH 10.0 with ammonia water, and water was added to make the total volume 100 ml. Then, 10 g of the cells collected above (wet cells) were added and allowed to react, with gentle stirring, at 30° C. for 3 days.

As a result, when the cells of the parent strain, *Brevibacterium flavam* MJ-233, were used, 1.1 g of L-asparaginic acid was obtained, while when the cells of the α-amino-n-butyric acid resistant strain, *Brevibacterium flavam* MJ-233-AB-41, were used, 3.2 g of L-asparaginic acid was obtained.

While the invention has been described in detail and with reference to specific embodiments thereof, it will be apparent to one skilled in the art that various changes and modifications can be made therein without departing from the spirit and scope thereof.

What is claimed is:

1. In a process for producing L-aspartic acid from fumaric acid or a salt thereof and ammonia or an ammonium salt, the improvement which comprises using a cultured product which is obtained by aerobically culturing a microorganism belonging to the Genus Brevibacterium and having resistance to α-amino-n-butyric acid.

2. The process of claim 1, wherein the microorganism is *Brevibacterium flavam* MJ-233-AB-41.

* * * * *